(12) United States Patent
Sachar et al.

(10) Patent No.: US 11,490,908 B2
(45) Date of Patent: Nov. 8, 2022

(54) THROMBECTOMY DEVICE AND METHODS OF USE

(71) Applicant: Contego Medical, Inc., Raleigh, NC (US)

(72) Inventors: Ravish Sachar, Raleigh, NC (US); Eugene Serina, Raleigh, NC (US); Hung Ha, Raleigh, NC (US); Dave Stern, Raleigh, NC (US)

(73) Assignee: Contego Medical , Inc., Raleigh, NC (US)

( * ) Notice: Subject to any disclaimer, the term of this patent is extended or adjusted under 35 U.S.C. 154(b) by 364 days.

(21) Appl. No.: 16/185,319

(22) Filed: Nov. 9, 2018

(65) Prior Publication Data

US 2019/0133616 A1 May 9, 2019

Related U.S. Application Data

(60) Provisional application No. 62/583,613, filed on Nov. 9, 2017.

(51) Int. Cl.
*A61B 17/22* (2006.01)
*A61B 17/221* (2006.01)
*A61B 17/00* (2006.01)

(52) U.S. Cl.
CPC ............ *A61B 17/22* (2013.01); *A61B 17/221* (2013.01); *A61B 2017/00778* (2013.01);
(Continued)

(58) Field of Classification Search
CPC .................. A61B 17/22; A61B 17/221; A61B 2017/2212; A61B 2017/22038;
(Continued)

(56) References Cited

U.S. PATENT DOCUMENTS 3,996,938 A * 12/1976 Clark, III ............. A61B 17/221
606/198
5,827,229 A 10/1998 Auth et al.
(Continued)

FOREIGN PATENT DOCUMENTS

| WO | 99/16362 A1 | 4/1999 |
| WO | 90/51505 A1 | 9/2000 |
| WO | 01/045592 | 6/2001 |

OTHER PUBLICATIONS

International Preliminary Report on Patentability. Issued by the International Bureau of WIPO in Application No. PCT/US2018/060074 dated May 22, 2020. 7 pages.
(Continued)

*Primary Examiner* — Darwin P Erezo
*Assistant Examiner* — Christian D Knauss
(74) *Attorney, Agent, or Firm* — Meunier Carlin & Curfman LLC

(57) ABSTRACT

The device disclosed herein is used to the remove a thrombus from the vasculature. It includes an aspiration catheter and a thrombus retrieval device that extends through the lumen of the aspiration catheter. An expandable braided assembly extends over a distal region of the retrieval device, and an activation wire extends through the lumen of the retrieval device to attach to and control the expansion of the braided assembly. Applying tension to the activation wire causes the braided assembly to expand to a diameter of the practitioner's choosing. For example, the practitioner may apply a first level of tension to the activation wire to deploy the braided assembly to a first diameter and then later change the diameter by applying a different level of tension. The expanded braided assembly contacts the thrombus and is pulled proximally toward the aspiration catheter to assist in thrombus removal.

18 Claims, 11 Drawing Sheets

(52) U.S. Cl.
CPC .............. *A61B 2017/00867* (2013.01); *A61B 2017/2212* (2013.01); *A61B 2017/22038* (2013.01); *A61B 2017/22079* (2013.01); *A61B 2017/22081* (2013.01)

(58) Field of Classification Search
CPC .. A61B 2017/22079; A61B 2017/0078; A61B 2017/22081; A61M 25/04; A61M 25/0074; A61F 2/013
See application file for complete search history.

(56) References Cited

U.S. PATENT DOCUMENTS

| | | | |
|---|---|---|---|
| 5,836,868 A * | 11/1998 | Ressemann | A61B 17/320725 606/159 |
| 5,972,019 A | 10/1999 | Engelson et al. | |
| 6,066,149 A * | 5/2000 | Samson | A61B 17/221 606/127 |
| 6,066,158 A | 5/2000 | Engelson et al. | |
| 6,673,042 B1 * | 1/2004 | Samson | A61M 29/02 604/104 |
| 6,695,858 B1 | 2/2004 | Dubrul et al. | |
| 6,699,260 B2 | 3/2004 | Dubrul et al. | |
| 6,800,080 B1 * | 10/2004 | Bates | A61B 17/221 606/127 |
| 7,931,659 B2 | 4/2011 | Bose et al. | |
| 8,366,735 B2 | 2/2013 | Bose et al. | |
| 8,460,312 B2 | 7/2013 | Bose et al. | |
| 8,758,364 B2 | 6/2014 | Eckhouse et al. | |
| 8,784,434 B2 | 7/2014 | Rosenbluth et al. | |
| 8,864,792 B2 | 10/2014 | Eckhouse et al. | |
| 9,005,237 B2 | 4/2015 | Eckhouse et al. | |
| 9,034,008 B2 | 5/2015 | Eckhouse et al. | |
| 9,119,656 B2 | 9/2015 | Bose et al. | |
| 9,149,609 B2 | 10/2015 | Ansel et al. | |
| 9,259,237 B2 | 2/2016 | Quick et al. | |
| 9,408,620 B2 | 8/2016 | Rosenbluth et al. | |
| 9,526,865 B2 | 12/2016 | Quick | |
| 9,597,101 B2 | 3/2017 | Galdonik et al. | |
| 9,655,633 B2 | 5/2017 | Leynov et al. | |
| 9,662,129 B2 | 5/2017 | Galdonik et al. | |
| 9,700,332 B2 | 7/2017 | Marchand et al. | |
| 9,717,514 B2 | 8/2017 | Martin et al. | |
| 9,801,643 B2 | 10/2017 | Hansen et al. | |
| 9,827,084 B2 | 11/2017 | Bonnette et al. | |
| 9,844,387 B2 | 12/2017 | Marchand et al. | |
| 9,883,877 B2 | 2/2018 | Look et al. | |
| 9,943,321 B2 | 4/2018 | Nita | |
| 10,004,531 B2 | 6/2018 | Rosenbluth et al. | |
| 10,463,386 B2 | 11/2019 | Ogle et al. | |
| 2001/0041899 A1 | 11/2001 | Foster | |
| 2003/0015206 A1 | 1/2003 | Roth et al. | |
| 2006/0058837 A1 | 3/2006 | Bose et al. | |
| 2006/0229645 A1 | 10/2006 | Bonnette et al. | |
| 2007/0016041 A1 | 1/2007 | Nita | |
| 2008/0228171 A1 * | 9/2008 | Kugler | A61B 17/221 604/529 |
| 2010/0204672 A1 | 8/2010 | Lockhart et al. | |
| 2010/0268264 A1 | 10/2010 | Bonnette et al. | |
| 2011/0054504 A1 | 3/2011 | Porter | |
| 2011/0160621 A1 | 6/2011 | Nita | |
| 2011/0152920 A1 | 7/2011 | Eckhouse et al. | |
| 2011/0172700 A1 | 7/2011 | Bose et al. | |
| 2011/0202088 A1 | 8/2011 | Eckhouse et al. | |
| 2011/0213403 A1 * | 9/2011 | Aboytes | A61M 29/02 606/194 |
| 2011/0319927 A1 | 12/2011 | Nita | |
| 2012/0022572 A1 * | 1/2012 | Braun | A61B 17/12045 606/194 |
| 2012/0078140 A1 | 3/2012 | Nita | |
| 2012/0116440 A1 | 5/2012 | Leynov et al. | |
| 2012/0150147 A1 | 6/2012 | Leynov et al. | |
| 2012/0330196 A1 | 12/2012 | Nita | |
| 2013/0325055 A1 | 12/2013 | Eckhouse et al. | |
| 2013/0325056 A1 | 12/2013 | Eckhouse et al. | |
| 2014/0155931 A1 | 6/2014 | Bose et al. | |
| 2014/0188127 A1 | 7/2014 | Dubrul et al. | |
| 2014/0188156 A1 | 7/2014 | Tekluve et al. | |
| 2014/0214067 A1 * | 7/2014 | Sachar | A61F 2/013 606/194 |
| 2014/0236219 A1 | 8/2014 | Dubrul et al. | |
| 2014/0243885 A1 | 8/2014 | Eckhouse et al. | |
| 2014/0324091 A1 | 10/2014 | Rosenbluth et al. | |
| 2014/0343585 A1 | 11/2014 | Ferrera et al. | |
| 2015/0018928 A1 | 1/2015 | Sachar et al. | |
| 2015/0127035 A1 * | 5/2015 | Trapp | A61B 17/320725 606/159 |
| 2015/0133918 A1 * | 5/2015 | Sachar | A61B 17/221 606/41 |
| 2015/0182361 A1 | 7/2015 | Ferrera et al. | |
| 2015/0238207 A1 | 8/2015 | Cox et al. | |
| 2015/0343663 A1 | 12/2015 | Mohanram et al. | |
| 2015/0352325 A1 | 12/2015 | Quick | |
| 2016/0120570 A1 * | 5/2016 | Kobayashi | A61B 90/39 606/166 |
| 2016/0143721 A1 | 5/2016 | Rosenbluth et al. | |
| 2016/0166265 A1 | 6/2016 | Nita | |
| 2016/0166266 A1 | 6/2016 | Nita | |
| 2016/0192957 A1 | 7/2016 | Okada | |
| 2016/0220346 A1 | 8/2016 | Bonnette et al. | |
| 2016/0262790 A1 | 9/2016 | Rosenbluth et al. | |
| 2016/0287276 A1 | 10/2016 | Cox et al. | |
| 2017/0079672 A1 | 3/2017 | Quick | |
| 2017/0105745 A1 | 4/2017 | Rosenbluth et al. | |
| 2017/0112514 A1 | 4/2017 | Marchand et al. | |
| 2017/0189041 A1 | 7/2017 | Cox et al. | |
| 2017/0215902 A1 | 8/2017 | Leynov et al. | |
| 2017/0216503 A1 | 8/2017 | Look et al. | |
| 2017/0290598 A1 | 10/2017 | Culbert et al. | |
| 2017/0325839 A1 | 11/2017 | Rosenbluth et al. | |
| 2017/0325931 A1 | 11/2017 | Bonnette et al. | |
| 2017/0333076 A1 | 11/2017 | Bruzzi et al. | |
| 2018/0064455 A1 | 1/2018 | Hansen et al. | |
| 2018/0092652 A1 | 4/2018 | Marchand et al. | |
| 2018/0028209 A1 | 5/2018 | Sudin et al. | |
| 2018/0193043 A1 | 7/2018 | Marchand et al. | |

OTHER PUBLICATIONS

Thrombectomy—Treating blocked veins by therapeutic medical device. Retrieved on-line at: https://www.youtube.com/watch?v=A04sa70HTkg, Published on Nov. 10, 2015.

International Search Report and Written Opinion issued for International Application No. PCT/US2018/060074, dated Jan. 24, 2019, 9 pages.

European Patent Office. Extended European Search Report, issued in EP Application No. 18876921.0 dated Jun. 23, 2021. 9 pages.

\* cited by examiner

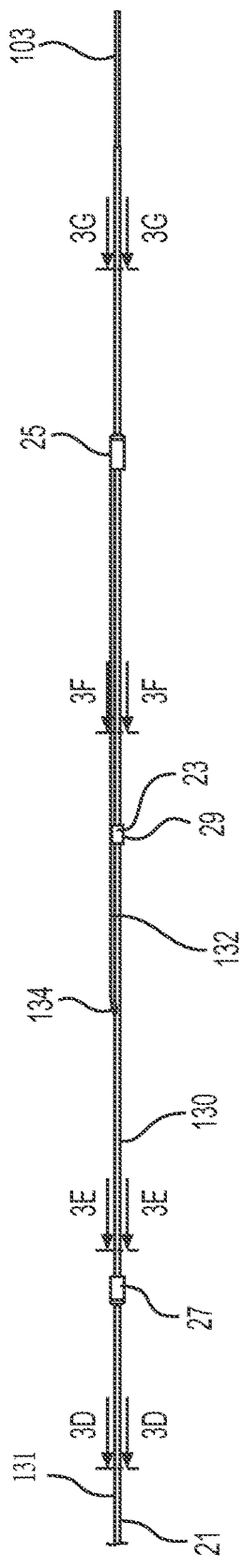

THROMBECTOMY DEVICE AND METHODS OF USE

CROSS REFERENCE TO RELATED APPLICATIONS

This application claims the benefit of U.S. Provisional Application 62/583,613, filed Nov. 9, 2017, which is incorporated by reference in its entirety for all purposes.

FIELD

This invention relates to a medical device for the removal of tissue from the body. One specific use of this device is removal of blood clots (thrombus) or plaque from arteries or veins.

BACKGROUND

It is often desirable to remove tissue from the body in a minimally invasive manner as possible, so as not to damage other tissues. For example, removal of tissue (e.g., blood clots) from the vasculature may improve patient conditions and quality of life.

Many vascular system problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Catheter directed thrombectomy and thrombolysis are commonly perceived to be less traumatic, less likely to decrease the morbidity and mortality associated with conventional surgical techniques. In recent years, direct administration of chemical lysing agents into the coronary arteries has shown to be of some benefit to patients who have thrombosed coronary arteries. In this procedure, a catheter is placed immediately in front of the blockage and a drip of streptokinase is positioned to be directed at the upstream side of the thrombus. Streptokinase is an enzyme which is able in time to dissolve the fibrin molecule. This procedure can take several hours and is not always successful in breaking up the thrombus. Furthermore, it can lead to downstream thrombus fragments (emboli) which can lead to blockage of small diameter branches.

Thrombectomy is a technique for mechanical removal of blood clots in an artery or vein. It refers to physically removing a clot as opposed to employing chemical lysis to dissolve it. Multiple devices have been introduced to break up and remove clot and plaque, but each has its own shortcomings. Specifically, the existing systems do not provide adequate methods for breaking up the clot into smaller pieces for subsequent aspiration. Also, they do not provide a method for removing the thrombectomy device over a guidewire and reinserting into the same location to complete the procedure. There is a need for an improved thrombectomy device that is more effective for removing thrombus and plaque from the vascular system.

SUMMARY

The devices and methods disclosed herein provide an improved thrombectomy device that achieves the objective of more efficient clot removal via improved intra-arterial geometry with over-the-wire functionality. The thrombectomy devices disclosed herein remove thrombi using braided assemblies that can be expanded to a diameter of the practitioner's choosing, enabling the practitioner to custom fit the device to the particular thrombus during the procedure. Unlike conventional thrombectomy devices, the diameter of the disclosed braided assembly can be changed mid-procedure as needed, for example, should additional grip be needed for removal of the thrombus. In some embodiments, multiple braided assemblies can be used to address longer thrombi. Each braided assembly can be separately expanded, such that the individual assemblies have different diameters during the procedure.

The aspiration catheter includes a proximal end and a distal end. The retrieval device extends through the lumen of the aspiration catheter and exits at the distal end. The retrieval device includes a proximal region, a distal region, and a first lumen extending between the proximal and distal regions. At least one braided assembly extends over a distal region of the retrieval device. The at least one braided assembly includes at least one slidable collar and a braid attached to the slidable collar. The braid can be one ply or two ply. The braid extends from the slidable collar toward a fixed attachment point that anchors the braid to the retrieval device. Upon expansion, the braid takes an elliptical or a spindle shape, having a maximum diameter near the center and narrowing as the proximal and distal regions approach the longitudinal axis of the braid.

At least one activation wire extends through the first lumen of the retrieval device and through an exit point located on the distal region. A distal end of the activation wire is attached to the slidable collar. In some embodiments, the exit point is a portal in a sidewall of the retrieval device.

The portal can be positioned beneath the braid of the braided assembly, for example. In some embodiments, the retrieval device includes a proximally located hypotube and a distally located support tube that has greater flexibility than the proximal hypotube. The portal can be defined in a sidewall of the distal support tube, and the braided assembly can be positioned over the distal support tube. In some embodiments, the distal support tube is attached to the distal end of the proximal hypotube.

Applying tension to the activation wire causes the braided assembly to expand to a diameter of the practitioner's choosing. As such, the braided assembly can be expanded to a range of expanded outer diameters by varying the level of tension on the activation wire. For example, the braided assembly is deployable to a first expanded outer diameter by placing a first level of tension on the activation wire, or to a second expanded outer diameter by placing a second level of tension on the activation wire. The practitioner may apply a first level of tension to the activation wire to deploy the braided assembly to a first diameter and then later change the diameter by applying a different level of tension. In some embodiments, the first level of tension in the activation wire is less than the second level of tension in the activation wire, such that the first expanded outer diameter is the maximum diameter of the braid in a partially expanded configuration, and the second expanded outer diameter is the maximum diameter of the braid in a fully expanded configuration. The expanded braided assembly contacts the thrombus and is pulled proximally toward the aspiration catheter to assist in thrombus removal. The braid has a shape memory of the collapsed configuration, so releasing tension in the activation wire allows the braid to relax to back to the collapsed state, for example, as it enters the aspiration catheter during removal.

Some embodiments of the thrombectomy device can further include a guidewire tubing. In some embodiments, the guidewire tubing can be shorter than the retrieval device. The retrieval device extends through the first lumen of the guidewire tubing, and the second lumen of the guidewire tubing extends over a guidewire. The fixed point of attachment of the braided assembly can be located on the guidewire tubing in some embodiments. The guidewire tubing can be shorter than the retrieval device in the longitudinal direction in some embodiments.

Some embodiments of the thrombectomy device can include a braided assembly with multiple braided sections and multiple sliding collars. In these embodiments, each additional slidable collar is positioned between two braided sections. Tensioning the activation wire causes at least partial expansion of each of the braided sections. The multiple braided sections can be formed of one continuous braid, or they can be formed of separate braids. In some embodiments, the activation wire is attached to one of multiple slidable collars. For example, the activation wire may be attached to the distal-most slidable collar.

Some embodiments of the thrombectomy device include at least one additional braided assembly and at least one additional activation wire. Each additional activation wire is attached to an additional slidable collar of an additional braided assembly, such that each braided assembly is separately expandable via an attached activation wire.

Some embodiments of the thrombectomy device include a proximally located tensioning element for controlling the activation wire that expands the braided assembly. The proximal end of the activation wire is attached to a tensioning element, which can be attached to a proximally located handle, for example.

Methods of performing thrombectomy procedures are also disclosed herein. The methods include advancing the distal end of the aspiration catheter through the vasculature to an area proximal to a thrombus, and advancing the distal end of the retrieval device carrying at least one braided assembly out of the distal end of the aspiration catheter and to a position distal to the thrombus. A first level of tension is applied to the activation wire that attaches to the braided assembly. The first level of tension moves the activation wire longitudinally within a lumen of the retrieval device, thereby moving the slidable collar of the braided assembly longitudinally over an exterior surface of the retrieval device and deploying the braided assembly to a first expanded outer diameter. If desired, a second level of tension, either greater or smaller than the first level of tension, can be applied to the activation wire. The second level of tension moves the activation wire longitudinally within the lumen of the retrieval device, thereby moving the slidable collar of the braided assembly longitudinally over the exterior surface of the retrieval device and deploying the braided assembly to a second expanded outer diameter. The distal end of the retrieval device maintains a stationary position as the slidable collar moves longitudinally over the exterior surface of the retrieval device and the braided assembly is expanded to the optimal diameter. In some embodiments, the second level of tension opens the braided assembly to a wider second expanded outer diameter to more firmly contact the thrombus with the braid. The thrombus is pulled toward the aspiration catheter and aspirated into the distal end of the aspiration catheter. In some embodiments, the thrombus is aspirated into the distal end of the aspiration catheter using an external vacuum source.

In some embodiments of the methods, the thrombus can be contacted and pulled using multiple braided sections or multiple braided assemblies. For example, movement of a single slidable collar can cause expansion of more than one braided section of a braided assembly. In another example, a proximally positioned braided assembly can collapse from a first expanded outer diameter to a narrower second outer diameter as it approaches the distal end of the aspiration catheter, while a distally positioned braided assembly can maintain an expanded outer diameter that is equivalent to or wider than the second outer diameter of the proximally positioned braided assembly.

Some embodiments of the methods can include the use of a guidewire. These methods include advancing the guidewire to a position distal to the thrombus prior to advancing the distal end of the retrieval device. The retrieval device can extend at least partially through a first lumen of a guidewire tubing, and the method includes advancing the guidewire tubing with the retrieval device over the guidewire. The activation wire moves longitudinally within the retrieval device, which is in the first lumen of the guidewire tubing. The guidewire moves longitudinally within a second lumen of the guidewire tubing.

DESCRIPTION OF DRAWINGS

FIG. 3C is a side view of the distal region of the thrombectomy device of FIG. 3A. The braided assembly is not included in this view.

FIG. 3D shows a cross sectional view taken along line 3D-3D of FIG. 3C.

FIG. 3E shows a cross sectional view taken along line 3E-3E of FIG. 3C.

FIG. 3F shows a cross sectional view taken along line 3F-3F of FIG. 3C.

FIG. 3G shows a cross sectional view taken along line 3G-3G of FIG. 3C.

DETAILED DESCRIPTION

Figure 1A:
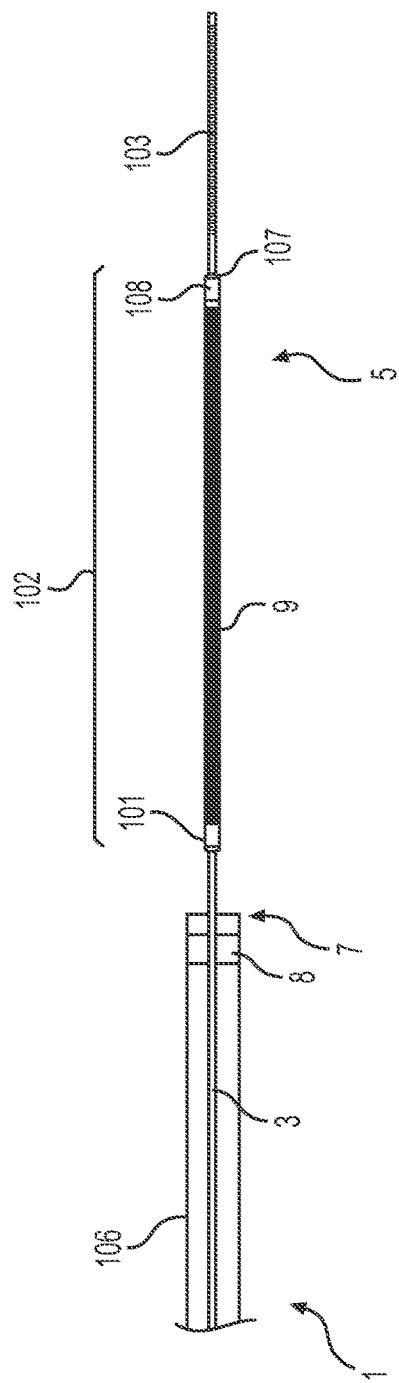
FIG. 1A is a side section view of an embodiment of the thrombectomy device having a single braided assembly in the collapsed configuration.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Certain terminology is used in the following description for convenience only and is not limiting. The words "right," "left," "lower," and "upper" designate direction in the drawings to which reference is made. The words "inner" and "outer" refer to directions toward and away from, respectively, the geometric center of the described feature or device. The words "distal" and "proximal" refer to directions taken in context of the item described and, with regard to the instruments herein described, are typically based on the perspective of the practitioner using such instrument, with "proximal" indicating a position closer to the practitioner and "distal" indicating a position further from the practitioner. The terminology includes the above-listed words, derivatives thereof, and words of similar import.

The thrombectomy devices disclosed herein remove a thrombus using a braided assembly that can be expanded to a diameter of the practitioner's choosing, enabling the practitioner to custom fit the device to the particular vessel and thrombus and during the procedure. Unlike conventional thrombectomy devices, the diameter of the disclosed braided assembly can be changed mid-procedure as needed. For example, the braided assembly can be opened to a wider diameter to apply more outward force against the thrombus should additional grip be needed for its removal. In some embodiments, multiple braided assemblies can be used to address longer thrombi. Each braided assembly can be separately expanded, such that the individual assemblies have different diameters during the procedure.

The device disclosed herein is used to the remove a thrombus, clot, or plaque from the veins or arteries of the body. It includes an aspiration catheter and a retrieval device that extends through the lumen of the aspiration catheter. An expandable braided assembly extends over a distal region of the retrieval device, such that when the retrieval device exits the distal end of the aspiration catheter, the braided assembly is positioned outside of the aspiration catheter. An activation wire extends through the lumen of the retrieval device. The distal end of the activation wire exits the retrieval device at an exit point to connect to and control the expansion of a braided assembly. On the proximal end, the activation wire is attached to a tensioning element. Applying tension to the activation wire causes the braided assembly to expand to a diameter of the practitioner's choosing. For example, the practitioner may apply a first level of tension to deploy the braided assembly to a first, partially expanded configuration and then later decide to widen the diameter to the fully expanded configuration by applying a greater level of tension to the activation wire. The expanded braided assembly contacts the thrombus, clot, or plaque and is pulled proximally toward the aspiration catheter to assist in removal. Hereinafter the device and methods will be described as removing (or being configured to remove) a thrombus. However, it will be understood that the device can also be used to remove clots or plaques from the vasculature with no structural (or only slight structural) modifications. Various embodiments of the thrombectomy catheter include a retrieval device with multiple braided assemblies, multiple activation wires, multiple braided sections of a single braided assembly, and retrieval devices with multiple lumens to, for example, enable use with a guidewire.

FIGS. 1A-1D show an embodiment of the thrombectomy device 1. FIG. 1A shows the aspiration catheter 106, the retrieval device 3, a collapsed braided assembly 102, and a guidewire tip 103. The aspiration catheter 106 is an elongated tube with reinforced construction that allows a vacuum to be applied at the proximal end to pull clot and emboli out of the artery or vein without collapsing. The aspiration catheter 106 can be formed of a polymer material. The aspiration catheter 106 can include an imaging marker 8 (such as a fluorescent or radiopaque marker) for use in imaging the position of the catheter during a procedure. Thrombus retrieval device 3 extends through aspiration catheter 106. The braided assembly 102 extends over a distal region 5 of the retrieval device 3, such that when the retrieval device 3 exits the distal end 7 of the aspiration catheter 106, the braided assembly 102 is positioned outside of the aspiration catheter 106. In the collapsed configuration, braided assembly 102 is sized and configured for insertion through the aspiration catheter 106 and into an artery or vein. Guidewire tip 103 extends distally from the distal end 107 of the retrieval device 3. The guidewire tip 103 can be flexible, shapeable, and steerable.

Figure 1B:
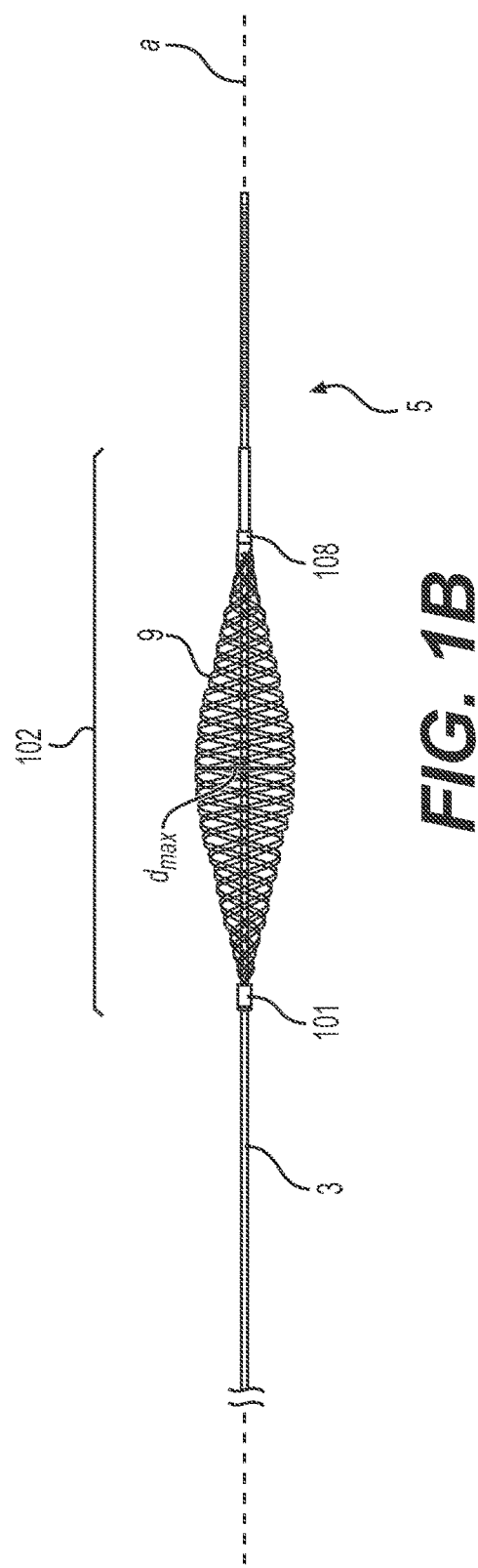
FIG. 1B is a side view showing the distal region of retrieval device the thrombectomy device carrying the braided assembly of FIG. 1A. The braided assembly is shown in an expanded configuration.

The braided assembly 102 is moveable from a collapsed to an expanded configuration. An example of a braided assembly 102 in an expanded configuration is shown in FIG. 1B, but the maximum diameter, $d_{max}$, of the expanded braided assembly 102 can be changed to any value over a continuous range, from a fully collapsed diameter, to a partially expanded diameter, to a fully expanded diameter. The maximum diameter of the braided assembly, $d_{max}$, is the widest point measured perpendicular to a longitudinal axis, a, extending through the center of the braided assembly 102. The braided assembly 102 can be sized and configured to disrupt and capture one or more clots, plaques, and/or thrombi and pull them toward the aspiration catheter 106 where they can be removed. The braided assembly 102 includes a braid 9, a slidable collar 108, and a fixed attachment point 101 where the braid 9 anchors to the retrieval device 3. The braid 9 may be attached directly to the retrieval device 3 at attachment point 101, or the braid 9 may be attached indirectly to the retrieval device 3 at attachment point 101. In some embodiments, the fixed attachment point 101 is a fixed collar that extends around the retrieval device 3, and the braid is welded, bonded, or otherwise adhered to the fixed collar. Regardless, at the fixed attachment point 101, the braid 9 does not move longitudinally relative to the retrieval device 3.

Figure 1C:
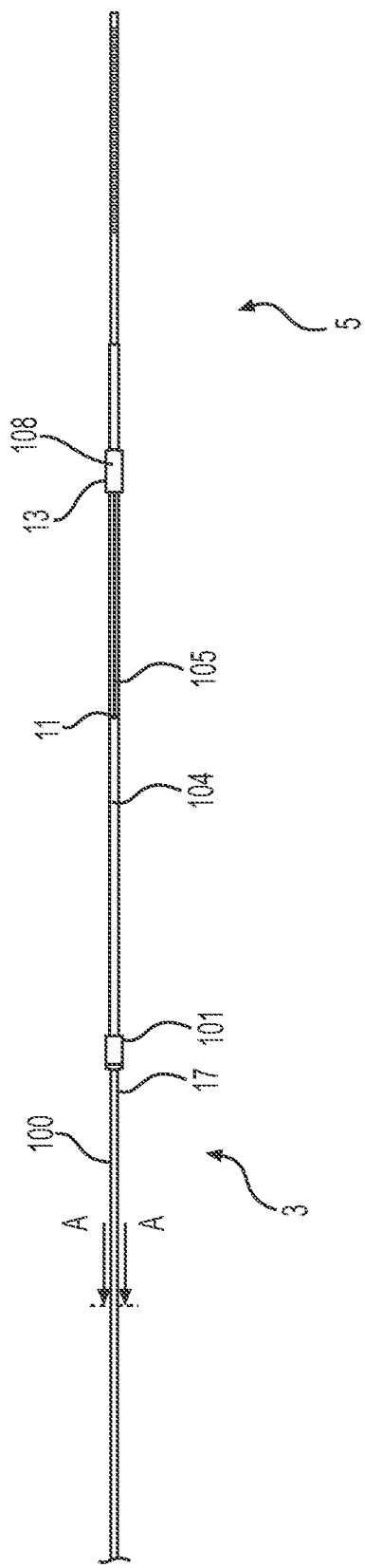
FIG. 1C is a side view showing the distal region of the thrombectomy device retrieval device of FIG. 1A. The braided assembly is not included in this view.

The opposite end of braid 9 is welded, bonded, or otherwise adhered to slidable collar 108. In the embodiments shown, the slidable collar 108 is slidably connected to the retrieval device 3 by virtue of its annular shape, which extends circumferentially around the retrieval device 3. The slidable collar 108 slides longitudinally along the retrieval device 3 as braid 9 is expanded and collapsed. The slidable collar 108 can be positioned distally to the fixed attachment point 101 (a distal position), as shown in FIGS. 1A-1C, or the slidable collar 108 can be positioned proximally to the fixed attachment point 101 (a proximal position). In some embodiments, slidable collar 108 or fixed attachment point 101 can include a marker that can be viewed using imaging modalities during a procedure. For example, the slidable collar 108 or fixed attachment point 101 can include a fluorescent or radiopaque label.

The braid 9 is composed of multiple strands of wire. The braid 9 takes an elliptical or a spindle shape when expanded, having a maximum diameter $d_{max}$ at or near the center of the braid 9 and narrowing as the braid approaches the fixed attachment point 101 and the slidable collar 108. The wires are formed of a shape memory material such as, but not limited to, shape memory polymers or shape memory metals (e.g., nitinol). The braid 9 has a baseline shape memory of the collapsed configuration, which forms a cylindrical structure around the retrieval device 3, as shown in FIG. 1A. In the activated, expanded configuration, the braid 9 has a tendency to relax toward the collapsed configuration.

When the practitioner is pulling a thrombus or plaque proximally toward aspiration catheter 106 using braided assembly 102, the braid 9 encounters distally oriented drag forces that are strongest along the widest portions (for example, the central region of the braid adjacent $d_{max}$). These drag forces resist the proximally oriented pulling force exerted by the practitioner. The distal end of braid 9 at slidable collar 108 will encounter less drag force while being pulled proximally because the radial force it exerts on the radially adjacent vasculature or thrombus is small, negligible, or non-existent. If the braid is not properly designed, the sliding collar 108 and distal end of the braid 9 will invert into the wider, central regions of the braid 9. Inversion during the procedure can be prevented by optimizing factors such as the pic count (crosses per inch), the wire diameter, the number of wires, and the ply of the braid (sets of overlapping braids). Higher pic counts increase flexibility, while lower pic counts increase longitudinal stiffness. Likewise, a braid with more than one ply (multiple sets of braids nested within each other), will be stiffer than a single-ply braid. Braids can be one-ply, two-ply, three-ply, or more. Braids with more wires will be stiffer than those with fewer wires, and braids with wider diameter wires will be stiffer than those with narrow diameter wires. Wires of varying diameters can be used within the same braid 9.

The design of the braided assemblies 102 disclosed herein may vary based on whether the device 1 is intended for an arterial procedure or for a venous procedure, since the procedure site will be wider in a venous setting. For example, a braid 9 designed for a venous application may have a $d_{max}$ of from about 0.8 inches to 1.2 inches, including about 0.8 inches, about 0.9 inches, about 1.0 inch, about 1.1 inches, and about 1.2 inches. For venous applications, a braid 9 may have a wire diameter range from about 0.005 inches to about 0.02 inches, including 0.005 inches, 0.0075 inches, 0.01 inches, 0.0125 inches, 0.015 inches, 0.0175 inches, and 0.02 inches. Different wires of the braid 9 may have different diameters, or they may have the same diameter. In some venous embodiments, the diameters of the wires of the braid 9 are 0.01 inches, 0.0125 inches, and/or 0.015 inches. Two-ply braids can utilize smaller wire diameters without sacrificing the radial force that can be applied. The pic count can be from 2 to 6 for venous applications. In some embodiments used in venous applications, the pic count is 3, 4, or 5. The number of wires per braid for a venous application can be anywhere from 8 to 40, including 8, 16, 24, 32, and 40.

Braids for venous applications were tested using a selection of the above listed venous application parameters. End points included the expansion force and the radial outward force applied by the braid to the inner surface of a tubing that simulates a vein (the tubing having an inner diameter of 24 millimeters). The expansion force is the force required to open the braid, as applied to the activation wire. The data is shown below in Table 1.

TABLE 1

Prototype testing for braids used in venous applications

| Prototype | Braid Ply | Wire Diameter (Inches) | # of Wires | Maximum Braid OD (inches) | Radial Outward Force in 24 mm ID tube (N) | Expansion force (N) |
|---|---|---|---|---|---|---|
| A | Double | 0.008 | 16 per ply (32 total) | 1.0 | 4.4 | 2.5 |
| B | Double | 0.010 | 16 per ply (32 total) | 1.0 | 5.5-6.6 | 6 |
| C | Single | 0.0125 | 24 | 1.0 | 8.6-9.9 | 10 |

For arterial applications, the braid 9 can have $d_{max}$ of from about 0.1 inches to about 0.4, including about 0.1 inches, about 0.12 inches, about 0.14 inches, about 0.18 inches, about 0.2 inches, about 0.22 inches, about 0.24 inches, about 0.28 inches, about 0.3 inches, about 0.32 inches, about 0.34 inches, about 0.36 inches, about 0.38 inches and about 0.4 inches. For example, the braid 9 can have a $d_{max}$ of about 0.28 inches, 0.3 inches, or 0.31 inches. The diameter of the wires of the braid 9 for an arterial application can range from about 0.001 inches to about 0.007 inches, including about 0.001 inches, about 0.002 inches, about 0.003 inches, about 0.004 inches, about 0.005 inches, about 0.006 inches, and about 0.007 inches. Different wires of the braid 9 may have different diameters, or they may have the same diameter. In some arterial embodiments, the diameters of the wires of braid 9 are 0.003 inches, 0.004 inches and/or 0.005 inches. Two-ply braids can utilize smaller wire diameters without sacrificing the radial force that can be applied. The pic count can be from 5 to 30 for arterial applications, including a pic count of 5, 6, 7, 8, 9, 10, 11, 12, 13, 14, 15, 16, 117, 18, 19, 20, 21, 22, 23, 24, 25, 26, 27, 28, 29 and 30. In some embodiments used in arterial applications, the pic count is 10, 12, or 15. The number of wires per braid 9 for an arterial application can be anywhere from 8 to 54, including 8, 16, 24, 32, 40, 48, and 54. In some embodiments, the number of wires per braid 9 for an arterial application is 26, 24, or 30.

Braids for arterial applications were tested using a selection of the above listed arterial application parameters. End points included the radial outward force applied by the braid to the inner surface of a tubing (the tubing having an inner diameter of 6 millimeters), and the proximal force needed to pull the braid through a restriction in the tubing (the inner diameter of the restriction being 4 millimeters). The tubing and the restriction simulate an artery and a thrombus/plaque, respectively. Favorable prototypes give a high radial outward force without requiring excessive force to pull the braid through the restriction. The data is shown below in Table 2. All braids tested were one-ply.

TABLE 2

Prototype testing for braids used in arterial applications

| Prototype | Wire Diameter (inches) | Pic count | # of Wires | Profile (Distal bond OD) (inches) | Maximum Braid OD (inches) | Radial Outward Force applied to 6 mm I.D. tubing (Newtons) | Force to pull through 4 mm ID Restriction (Newtons) |
|---|---|---|---|---|---|---|---|
| A | 0.004 | 10 | 16 | 0.050 | 0.28 | 0.8 | 1.8 |
| B | 0.004 | 15 | 24 | 0.053 | 0.28 | 1.0 | 2.8 |
| C | 0.005 | 10 | 16 | 0.054 | 0.31 | 1.5 | 3.2 |
| D | 0.005 | 10 | 24 | 0.058 | 0.31 | 1.6 | 4.1 |
| E | 0.006 | 10 | 16 | 0.060 | 0.31 | 1.7 | 4.4 |
| F | 0.006 | 12 | 16 | 0.063 | 0.30 | 1.8 | 4.6 |
| G | 0.002 | 24 | 48 | 0.073 | 0.31 | 0.8 | 1.9 |
| H | 0.003 | 24 | 48 | 0.078 | 0.31 | 1.8 | 3.5 |
| I | 0.004 | 12 | 24 | 0.054 | 0.31 | 1.9 | 2.6 |

Figure 1D:
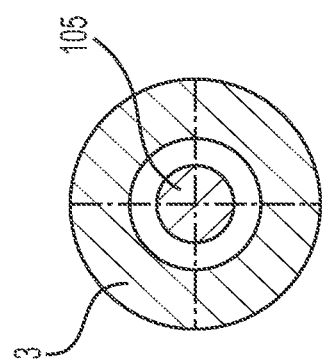
FIG. 1D is a cross sectional view of the embodiment of FIG. 1A, taken along lines A-A of FIG. 1C.

The activation wire 105 extends through the lumen of the retrieval device 3, exits the retrieval device 3 at exit point 11, and extends distally along the exterior surface of the retrieval device 3. The distal end 13 of the activation wire 105 is attached to slidable collar 108. As such, the activation wire 105 is able to control the expansion and collapse of the braid 9 via the slidable collar 108. The distance between exit point 11 and slidable collar 108 affects the length that the slidable collar can be pulled along retrieval device 3 to open the braided assembly 102. If it is too close to slidable collar, the braided assembly 102 will not be able to open fully. As such, exit point 11 should be positioned proximally far enough from the unexpanded position of slidable collar 108 to enable the braided assembly 102 to open to its maximum outer diameter. FIG. 1C shows the embodiment of FIGS. 1A and 1B without braid 9 to facilitate viewing the activation wire 105 and the activation wire exit point 11. FIG. 1D is a cross sectional view of activation wire 105 in retrieval device 3, taken at line A-A of FIG. 1C. The internal positioning of the proximal regions of the activation wire 105 (within retrieval device 3) is advantageous in that no friction or bulk is added by the system that controls expansion of the braided assembly 102.

The proximal region of activation wire 105 (not shown) may be tensioned and released to control the expansion and collapse of the braided assembly 102 via movement of slidable collar 108. Under tension, the activation wire 105 moves proximally within the lumen of the retrieval device 3 as it translates the tension from the proximal region of the activation wire 105 to the braided assembly 102. In implementations where the slidable collar 108 is in the distal position (as shown), the exit point 11 of the activation wire is located proximally to the slidable collar 108. The exit point 11 can be, for example, a portal in the sidewall of retrieval device 3. Use of a slidable collar 108 to expand the braided assembly 102 is advantageous because the distal end of the braided assembly 102 can be moved while the distal region 5 of the retrieval device 3 maintains a constant position within the vasculature. Maintaining a constant position of the distal region 5 of retrieval device 3 is advantageous because sliding proximal/distal movement of the distal region 5 within the vessel can result in vessel damage or perforation.

In implementations where the slidable collar 108 is in the proximal position relative to the fixed attachment point (not shown), the activation wire 105 extends distally past the slidable collar 108 inside the retrieval device 3, exits the retrieval device 3 at exit point 11, then doubles back and extends along the exterior surface of the retrieval device 3 to attach to the proximally located slidable collar 108. The exit point 11 can be a portal in the sidewall of the retrieval device as described above, or the exit point 11 can be the distal end 107 of the retrieval device 3.

Retrieval device 3 can include a proximal hypotube 100 and a distal support tube 104, as shown in FIG. 1C. In some embodiments, the hypotube 100 extends through the support tube 104. However, the distal region can be made more flexible by attaching the proximal end of the distal support tube 104 to the distal end 17 of the proximal hypotube 100 (for example, by adhesive bonding, heat bonding, or welding processes). The fixed attachment point 101 of the braided assembly 102 can be located on distal support tube 104 and the slidable collar 108 can extend around the distal support tube 104, such that the braided assembly 102 is positioned over and around the distal support tube 104. The braided assembly 102 can alternatively be positioned only partially over the distal support tube (i.e., one of the fixed attachment point 101 or the slidable collar 108 is attached to the proximal hypotube 100, and the other of the fixed attachment point or the slidable collar 108 is attached to the distal support tube 104). In some embodiments, the support tube 104 serves to increase the overall diameter of the retrieval device 3, for example, to accommodate a larger diameter braid and to encapsulate the guidewire tip 103. The distal support tube 104 can also provide a lower friction surface for movement of the slidable collar 108 than the proximal hypotube 100 would provide.

In some embodiments, distal support tube 104 has greater flexibility than the proximal hypotube 100. For example, the distal support tube 104 can be made of a polymer material, while the proximal hypotube 100 is made of a more rigid metal material. In some embodiments, the proximal hypotube 100 is constructed from metal hypodermic needle tubing. The hypotube 100 can be up to 50 times stiffer than the support tube 104. There are several advantages to having a distal support tube 104 with greater flexibility than proximal hypotube 100. The greater flexibility of the support tube 104 enables a gradual transition in flexibility between the hypotube 100 and the guidewire tip 103. In some scenarios, the greater flexibility of the distal support tube 104 can facilitate movement of the braided assembly 102 through a tortuous thrombus. The greater flexibility can promote kink resistance. The greater flexibility of the distal support tube 104 can also facilitate the introduction of a portal or exit point 11 during the production of the device. The higher rigidity of the hypotube 100 (as compared to support tube 104) is important because it allows the retrieval device 3 to be pushed through the vasculature. The rigidity of hypotube 100 also helps to ensure that the braided assembly 102 can be pushed through a thrombus or plaque.

On the proximal end, the activation wire 105 can be attached to a tensioning element (not shown) that allows the activation wire 105 to be moved forward or retracted backward within the retrieval device 3. Applying tension to the activation wire 105 causes the slidable collar 108 to move and causes the braided assembly 102 to expand to a diameter of the practitioner's choosing. Similarly, releasing tension on the activation wire 105 allows the braided assembly 102 to relax into the collapsed, baseline configuration.

Figure 2:
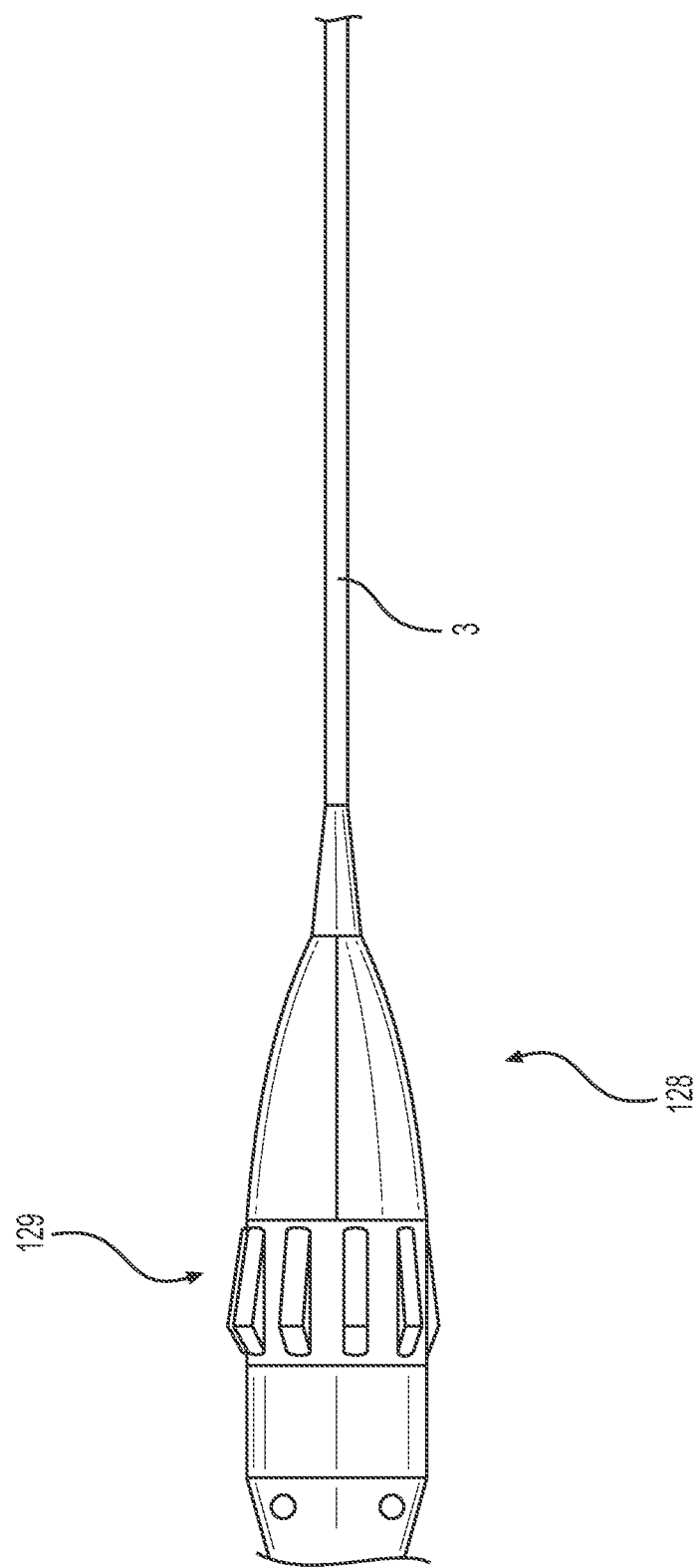
FIG. 2 shows a side view of an embodiment of a handle that can be used to control expansion and retraction of a braided assembly.

In some embodiments, such as the one shown in FIG. 2, the device includes a proximal handle 128. The handle 128 is coupled to a proximal end of retrieval device 3. The tensioning element is a knob 129 that is coupled to the proximal end of activation wire 105 on the inside of the handle. Actuation of the knob 129 in one direction causes the activation wire 105 to be tensioned (expanding the braided assembly), and actuation of the knob 129 in the opposite direction releases tension on the activation wire 105 (collapsing the braided assembly). In other embodiments, the tensioning element can include a slider, racheting mechanism, or lever. The aspiration catheter 106 terminates in a y-adaptor (not shown) that separates the lumen of the aspiration catheter to be connected to a vacuum source for removal of the clot or emboli and allows the activation wire to be connected to the handle 128.

Figure 7A:
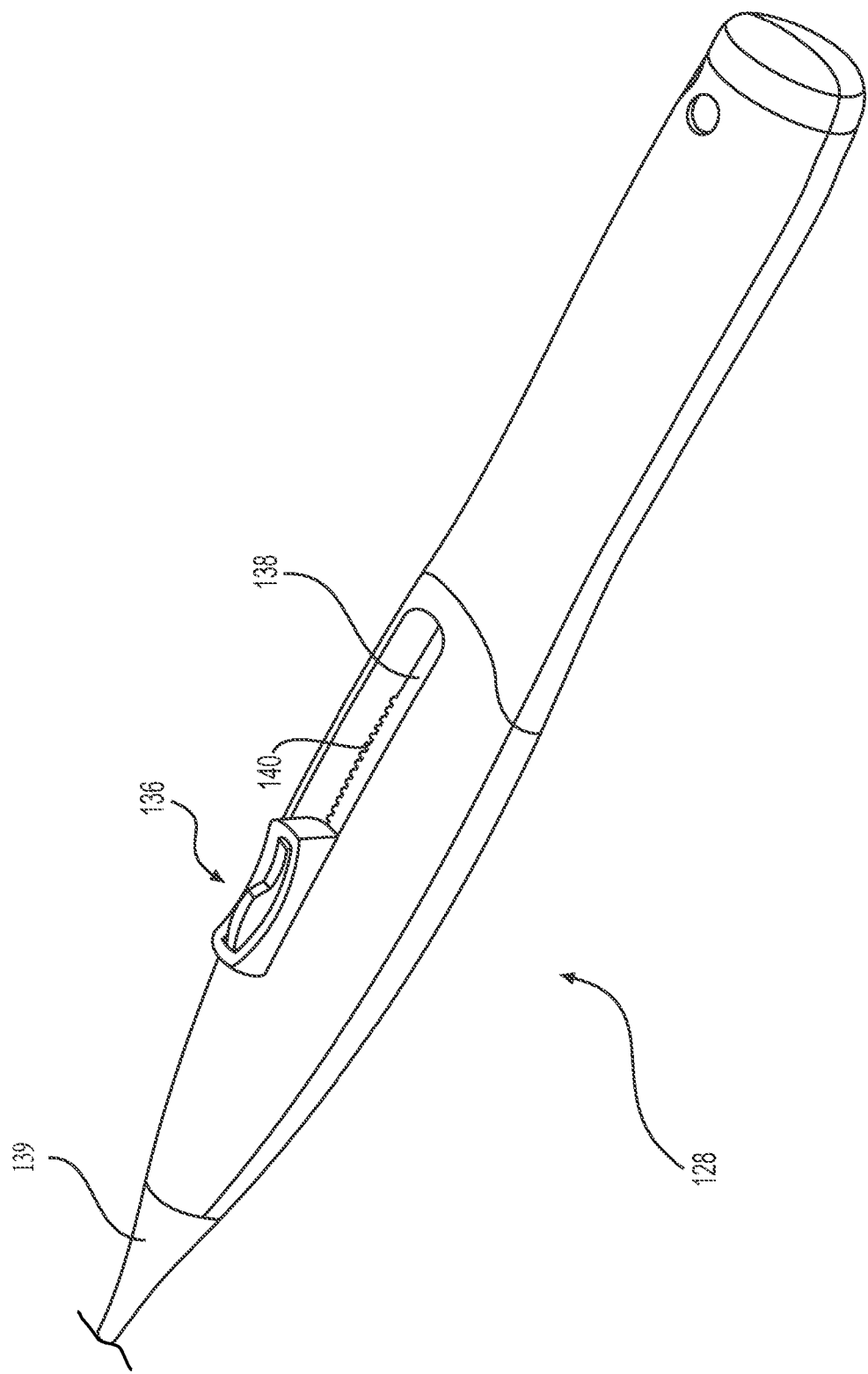
FIG. 7A shows a perspective view of another embodiment of a handle that can be used to control expansion and retraction of a braided assembly.
Figure 7B:
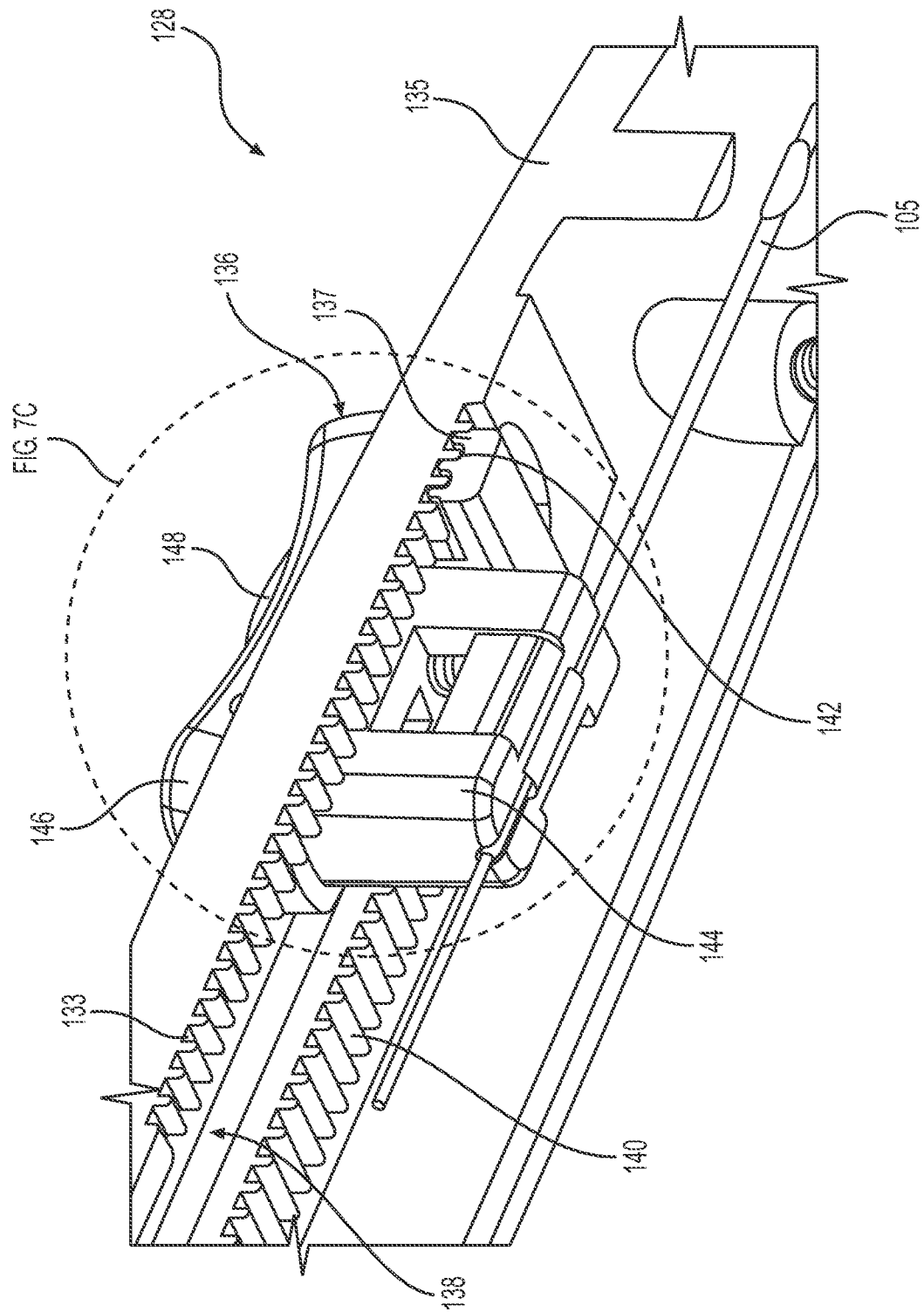
FIG. 7B shows a bottom up, inside view of the locking slider of the handle embodiment of FIG. 7A.
Figure 7C:
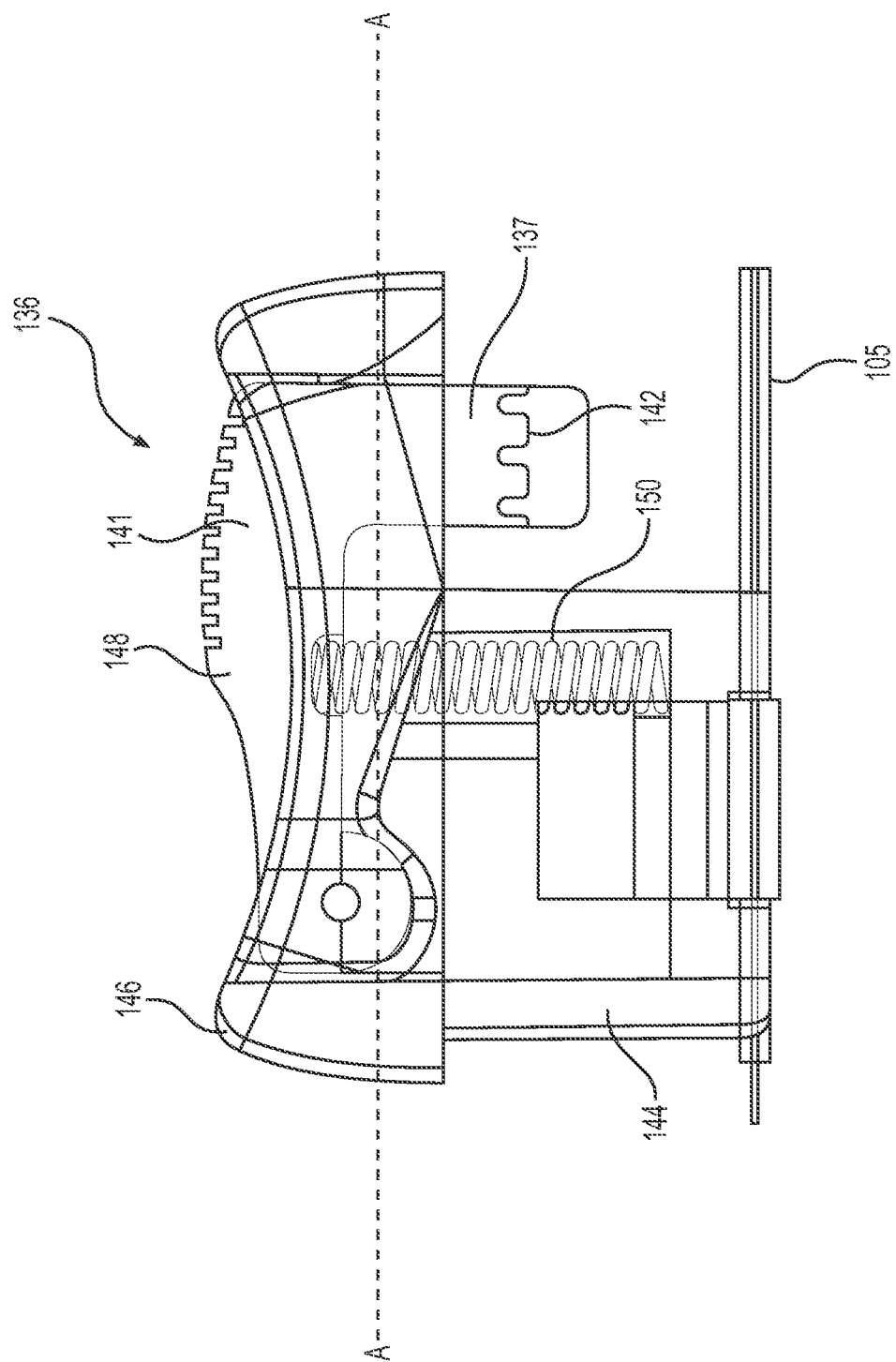
FIG. 7C shows a cross section of the locking slider circled in FIG. 7B.

Another embodiment of a proximal handle 128 is shown in FIGS. 7A-7C. The handle 128 of FIGS. 7A-7C is advantageous in that it enables a practitioner to lock the braided assembly 102 at a fixed outer diameter. This can be useful, for example, when pushing and pulling the device through a thrombus. As shown in FIG. 7A, proximal handle 128 is coupled to a proximal end of retrieval device 3. Activation wire 105 extends proximally past the proximal end retrieval device 3 and into proximal handle 128. Strain relief section 139 is formed of a flexible material that prevents kinking of the retrieval device 3 just distal to the handle 128. Proximal handle 128 also includes a tensioning element in the form of locking slider 136, which slides proximally and distally within groove 138 and can be locked in place to secure the outer diameter of the braided assembly 102 during a procedure. The underside of locking slider 136 and groove 138 is shown in FIG. 7B, and a cross sectional view of locking slider and groove 138 is shown in FIG. 7C. Locking slider 136 includes a sliding portion 146 and a lock button 148. As seen in FIG. 7B, downward pointing teeth 140 extend downward from the inner surface 133 of the outer casing 135 of handle 128, from a position adjacent the groove 138. The lock button 148 includes an exterior portion 141 with a textured gripping surface. The lock button 148 extends downward through sliding portion 146, and includes an interior portion 137. The interior portion 137 of the lock button 148 extends away from the exterior portion 141 of lock button 148 in a direction that is perpendicular to the longitudinal axis A-A of the locking slider 136. Interior portion 137 includes upward facing teeth 142 that are configured to engage with the downward facing teeth 140 of the outer casing 135 of the handle 136. Spring 150, which is vertically positioned within slider 146, beneath the exterior surface 141 of lock button 148, exerts an upward force on lock button 148 to hold the upward facing teeth 142 in a locked configuration with the downward facing teeth 140 of the outer casing 135. When lock button 148 is compressed, the spring 150 is compressed and the teeth 140, 142 disengage. With the lock button 148 pressed and the teeth 140, 142 disengaged, proximal or distal force can be applied to sliding portion 146 to move the locking slider 136 within the groove 138. An interior portion 144 of the sliding portion 146 grips the activation wire 105. As the locking slider 136 is moved within groove 138, the activation wire 105 is moved proximally or distally to affect the expansion or allow the collapse of the braided assembly 102.

Conventional thrombectomy devices utilize shape memory elements with a baseline expanded configuration. These conventional devices risk inadvertent overexpansion and damage to the vessel. Furthermore, conventional devices are often restrained by a bulky overlying sheath, which is pulled back to allow the device to self-expand.

Advantageously, using a device with a shape memory of the collapsed position reduces the risk of overexpansion and injury during self-expansion. Self-collapse also allows the device to be restrained using the low-profile activation wire system described herein. An additional advantage is the ability to expand the braided assembly to various diameters to precisely custom fit the size of the vessel. This can be especially useful if the size of the vessel is different than originally anticipated. The level of grip between the braid 9 and the surrounding thrombus can also be customized as needed by applying different levels of tension to the activation wire 105. For example, the practitioner may apply a first level of tension to deploy the braided assembly 102 to a first expanded outer diameter to contact the thrombus. If the force between the thrombus and the braid 9 is not enough to pull the thrombus toward the aspiration catheter 106, the practitioner can widen the braid 9 to a second expanded outer diameter by applying a greater second level of tension to the activation wire 105. This widened diameter provides a greater contact force between the thrombus and the braid 9, such that the thrombus can be more easily pulled toward aspiration catheter 106.

Figure 3A:
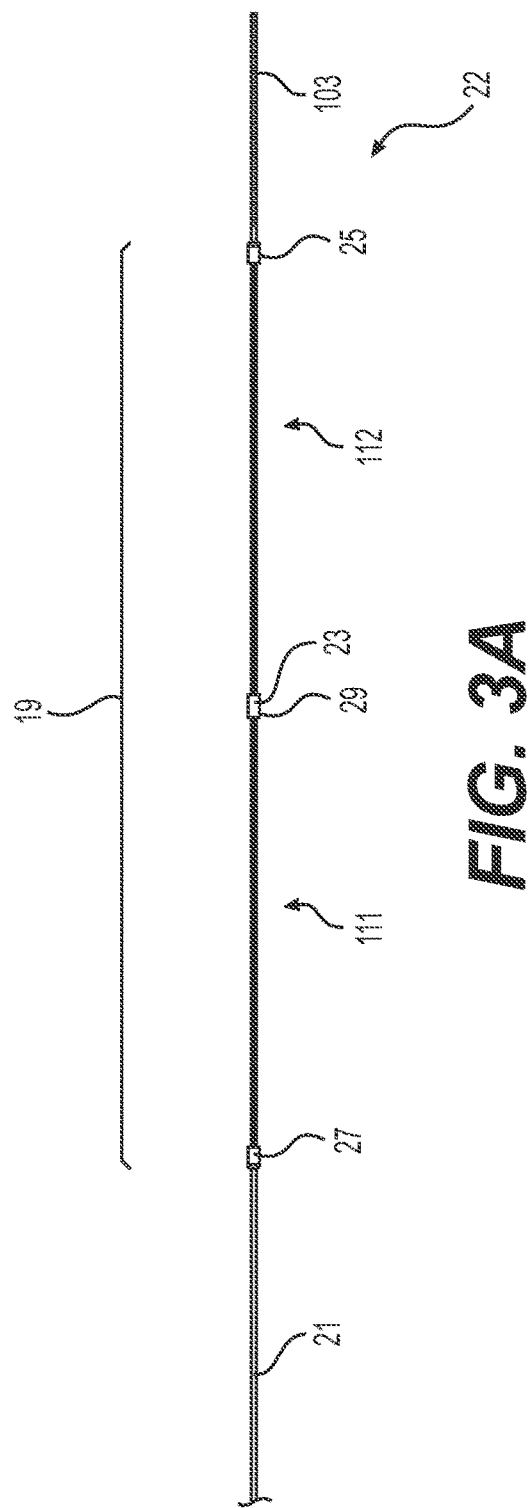
FIG. 3A is a side view of a distal region of an additional embodiment of the thrombectomy device in an unexpanded configuration. The embodiment has a braided assembly having multiple braided sections.
Figure 3B:
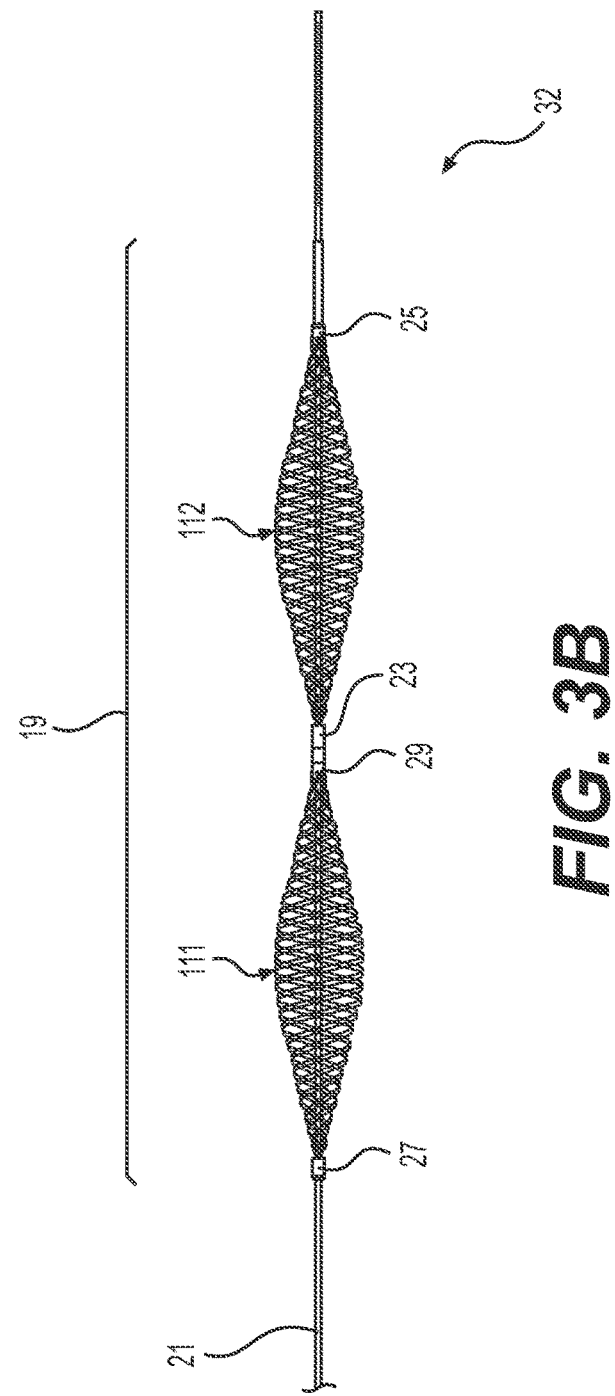
FIG. 3B is a side view of the distal region of the embodiment of FIG. 3A in an expanded configuration.

FIGS. 3A-3D show an additional embodiment of a thrombectomy device having a braided assembly 19 with multiple braided sections 111, 112. The elongated nature of this embodiment facilitates the capture and retrieval of long thrombi. As shown in FIG. 3A and FIG. 3B, ach of the braided sections 111, 112 is attached to and extends around the distal region 22 of retrieval device 21. The braided assembly 19 includes multiple sliding collars 23, 25 and a fixed attachment point 27. Proximal braided section 111 is attached to and extends between the fixed attachment point 27 and the proximal slidable collar 23, where it is welded, bonded, or otherwise adhered at a central sliding attachment point 29. Distal braided section 112 is attached to and extends between the proximal slidable collar 23 and the distal slidable collar 25. In some embodiments, the braided sections are formed by constraining one larger braid with the proximal slidable collar 23. In other embodiments, each braided section is formed from a separate braid (such that each of the proximal and distal braided assemblies are separately fixedly attached to proximal slidable collar 23). In some embodiments, the slidable collars 23, 25 can be positioned distally to the fixed attachment point 27, as illustrated in FIG. 3A. In other embodiments, the slidable collars can be positioned proximally to the fixed attachment point (not shown). Though illustrated with two braided sections 111, 112, other embodiments of the braided assembly 19 could include more than two braided sections and more than two slidable collars.

FIG. 3C shows the thrombectomy device of FIGS. 3A and 3B without the braided assembly 19. Retrieval device 21 has a hypotube 131 fixedly attached to a support tube 130. A single activation wire 132 extends through hypotube 131 and support tube 130 to an exit point 134 positioned on the support tube 130. From there, it travels along the outer surface of support tube 130, running beneath proximal sliding collar 23 to attach to distal sliding collar 25. Cross sectional views shown in FIG. 3D, FIG. 3E, FIG. 3F, and FIG. 3G show the radial position of activation wire 132 with respect to hypotube 131, the support tube 130, and the guidewire tip 103 at various axial locations along the thrombectomy device shown in FIG. 3C. The activation wire 132 is utilized to control expansion of the braided assembly via connection to the distal sliding collar 25. In other embodiments, the activation wire 132 can be attached to the proximal sliding collar 23. retrieval deviceProximal movement of the proximal slidable collar 23 or the distal slidable collar 25 by the activation wire generates a force on the other of the two slidable collars, such that the two braided sections 111, 112 are expanded (or partially expanded) in unison. As described above, the braids are formed of a shape memory material with a bias toward the collapsed configuration, so that tensioning the activation wire enables multiple levels of expansion.

Figure 4:
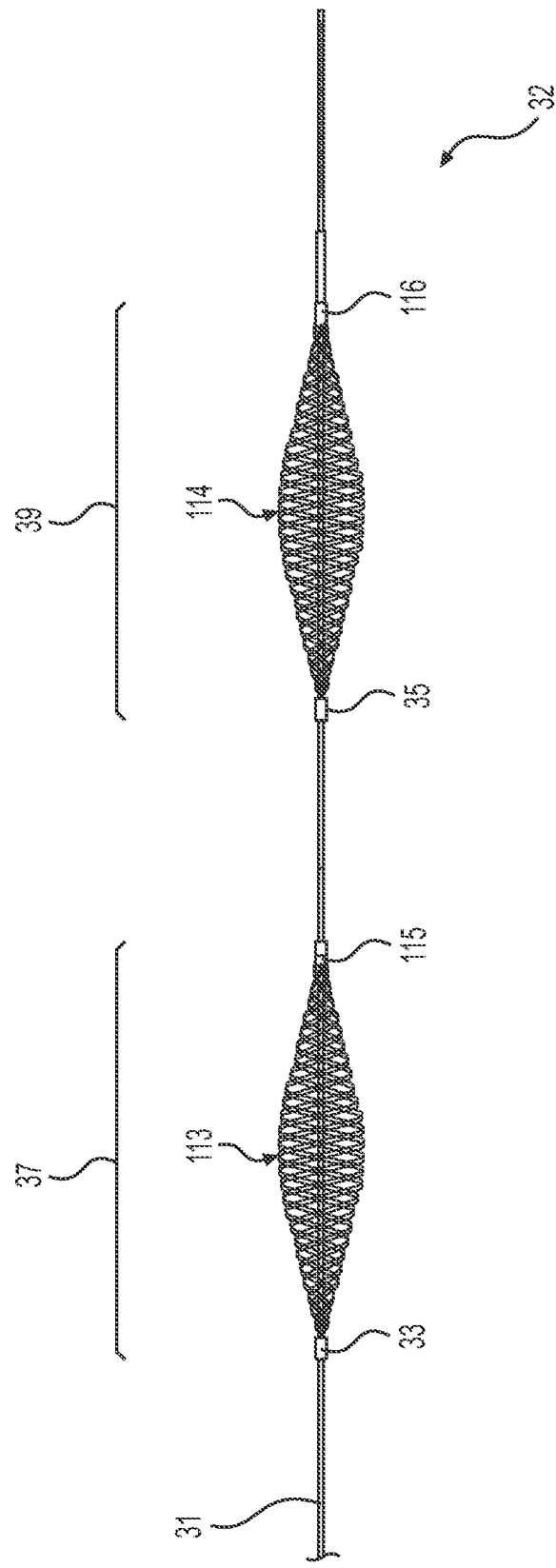
FIG. 4 shows an additional embodiment of the thrombectomy device having multiple expandable braided assemblies.

FIG. 4 shows an additional embodiment with multiple, separately expandable braided assemblies 37, 39. The braided assemblies 37, 39 are spaced from each other along the distal region 32 of retrieval device 31. The proximal braided assembly 37 includes braided section 113 that extends between a fixed attachment point 33 and a slidable collar 115. The distal braided assembly 39 includes braided section 114 that extends between a fixed attachment point 35 and a slidable collar 116. Each braided assembly is controlled by a separate activation wire, such that each braided assembly can be individually controlled. Each activation wire exits the retrieval device 31 from an exit point beneath the individual braid and attaches to the individual slidable collar (not shown). The multiple activation wires can travel through the same lumen in retrieval device 31, or they could have individual lumens. Depending upon the positioning of the slidable collars in relation to the fixed attachment points, in some embodiments, each additional activation wire can travel through the same lumen and exit the retrieval device at the same portal, or at different portals. In some embodiments, one or more activation wires can exit from the distal end of the retrieval device 31.

As with the previously described embodiments, the braids of the embodiment shown in FIG. 4 are formed of a shape memory material with a bias toward the collapsed configuration, such that tensioning the activation wire enables deployment of the braid to a range of diameters. Each braided assembly is deployable to a partially expanded configuration by placing a first level of tension in the attached activation wire, or to a fully expanded configuration by placing a second, greater level of tension into the activation wire. Thus, when multiple activation wires and braided assemblies are used, a first braided assembly can be deployed to a partially expanded state while a second braided assembly is deployed in a fully expanded state. In some scenarios, it may be advantageous for one braided assembly to be fully collapsed while another braided assembly is either partially or fully expanded. This can be advantageous, for example, when pulling a longer thrombus into the aspiration catheter 106. The proximal braided section 113 can be collapsed as it enters the aspiration catheter, prior to the distal braided section 114 which is still outside of the aspiration catheter.

In some embodiments, braids of separate braided sections or separate braided assemblies can have different properties, such as different maximum expanded diameters, different wire sizes, different wire densities, different numbers of wires, etc. These properties can vary depending upon the positioning of the braided section or the braided assembly along the retrieval device. For example, the distal braided section or braided assembly might have a larger expanded diameter to better pull back against the thrombus, while the proximal braided section(s) or braided assembly(s) might be less dense and stronger to better engage the middle of the thrombus.

Figure 5A:
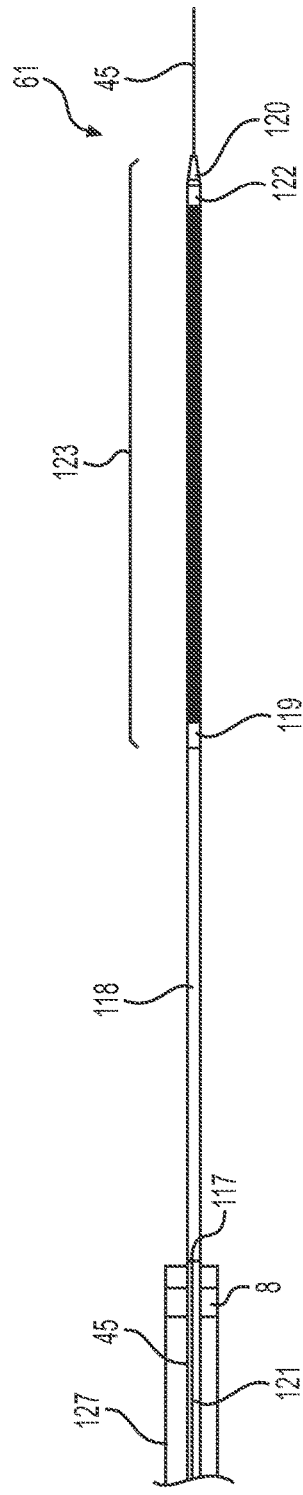
FIG. 5A shows a side section view of an embodiment of the thrombectomy device that enables use with a guidewire.
Figure 5B:
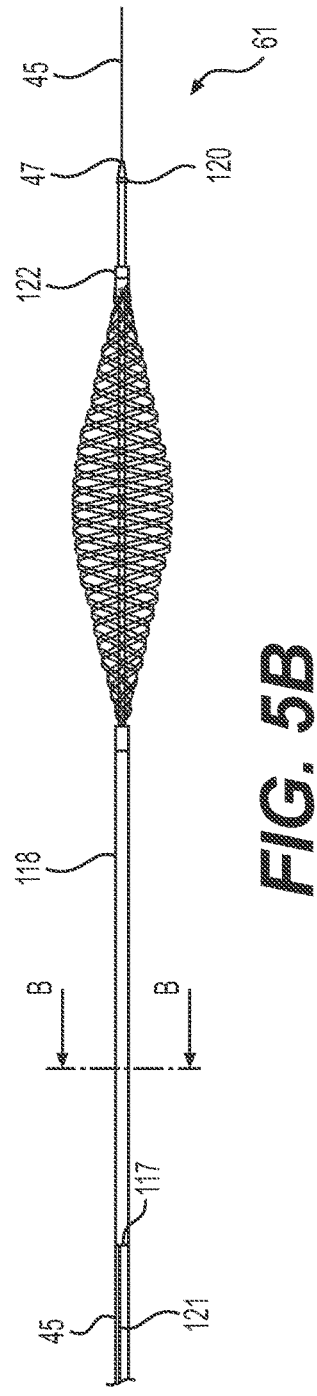
FIG. 5B shows the embodiment of FIG. 5A in an expanded configuration.
Figure 5C:
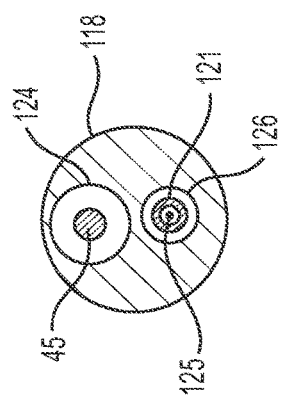
FIG. 5C is a cross section of the embodiment of FIGS. 5A and 5B, taken along line B-B of FIG. 5B.

FIGS. 5A-5C show an embodiment of the thrombectomy device that enables use with a guidewire, such that a practitioner can remove and reinsert the device to the same anatomic position multiple times (for example, to clean the device during the procedure). FIG. 5A shows aspiration catheter 127, retrieval device 121, guidewire tubing 118, braided assembly 123 (in the collapsed configuration), and guidewire 45. Guidewire tubing 118 is positioned around the distal region 61 of retrieval device 121. The guidewire tubing 118 is shorter than the retrieval device 121 in the longitudinal direction, such that the guidewire 45 leaves the guidewire tubing 118 at the proximal guidewire exit 117 and extends alongside retrieval device in a proximal direction. FIG. 5B shows the embodiment of FIG. 5A with the braided assembly 123 in an expanded state. As shown in the cross section of FIG. 5C taken at line B-B of FIG. 5B, guidewire 45 extends through the first lumen 124 of the guidewire tubing 118. The guidewire 45 exits guidewire tubing 118 at distal guidewire exit 47. The guidewire tubing 118 can include a distal atraumatic tip 120. The guidewire tubing 118 can be formed, for example, of a polymer material. Retrieval device 121, including activation wire 125, extends through a second lumen 126 of the guidewire tubing 118. As described above, the activation wire 125 is connected on the proximal end to a tensioning element, extends through retrieval device 121 to an exit point, leaves the retrieval device 121 at the exit point (beneath the braid), and attaches at its distal end to the slidable distal collar 122 on the braided assembly 123. The exit point can be, for example, a tunnel through the sidewalls of the retrieval device 121 and the guidewire tubing 118 (i.e., a tunnel formed by a portal in the sidewall of the retrieval device 121 that is aligned/coaxial with a portal in the sidewall of the guidewire tubing 118). In use, the guidewire tubing 118 and the retrieval device 121 are introduced together over the previously placed vascular guidewire 45. Because the guidewire 45 is retained within the guidewire tubing 118, it is pulled at least partially to the side within the lumen of aspiration catheter 127 and can move without interfering with activation wire 125. The guidewire tubing 118 and the retrieval device 121 keep the activation wire 125 and the guidewire 45 moving in an axial direction, independently from one another, using a low-profile and low-friction design. Once in position, the braided assembly 123 is expanded and the proximal end of the aspiration catheter 127 is connected to a vacuum source. The braided assembly 123 is expanded and then retracted back toward the aspiration catheter 127, pulling the clot with it and breaking it into small pieces.

Figure 6A:
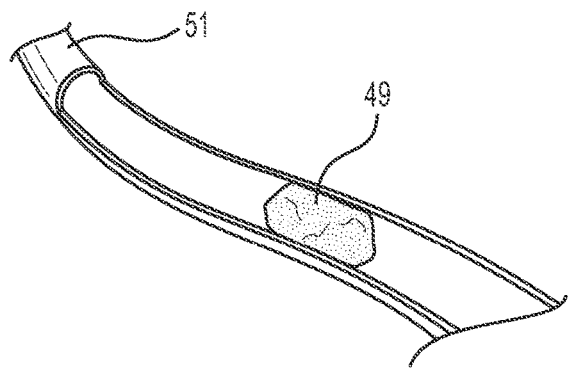
FIGS. 6A-6F show an example method of using a thrombectomy device.

Methods of performing thrombectomy procedures are also disclosed herein. An example method is illustrated in FIGS. 6A-6F. FIG. 6A illustrates thrombus 49 occluding vessel 51. Distal end of aspiration catheter 53 is advanced through the vasculature to an area proximal to the thrombus 49, as shown in FIG. 6B. The distal end of retrieval device 55 carrying braided assembly 57 is advanced out the distal end of the aspiration catheter 53 and through thrombus 49, such that the braided assembly 57 is distal to thrombus 49, as shown in FIG. 6C. The practitioner then places tension in the activation wire housed inside the retrieval device 55, thereby moving the activation wire longitudinally within the lumen of the retrieval device and moving the slidable collar of the braided assembly longitudinally over the exterior surface of the retrieval device. Movement of the slidable collar via the activation wire causes braided assembly 57 to expand to the diameter of the practitioner's choosing. Should the practitioner wish to alter the level of expansion during the procedure (i.e., change the maximum diameter d of the braided assembly 57), this is made possible by altering the level of tension in the activation wire, which again moves the activation wire within the retrieval device and moves the slidable collar, as described above. Advantageously, the distal end of the retrieval device 55 maintains a stationary position as the braided assembly is expanded to the optimal diameter. Maintaining a constant position of the distal end of retrieval device 55 is advantageous because sliding proximal/distal movement of the distal end within the vessel can result in vessel damage or perforation.

Figure 6D:
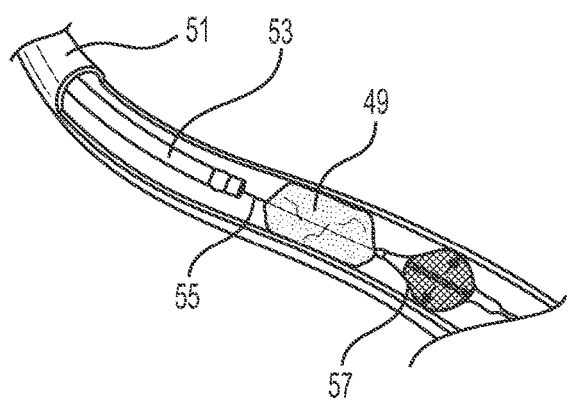
Figure 6B:
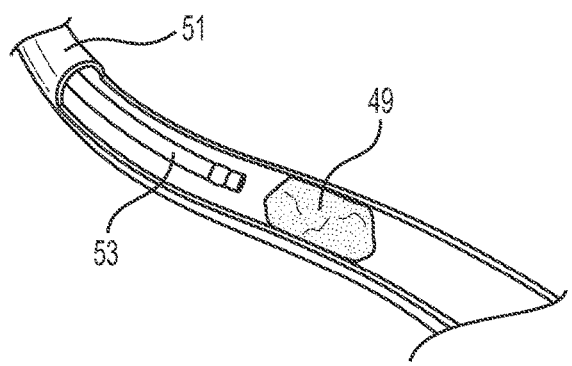
Figure 6E:
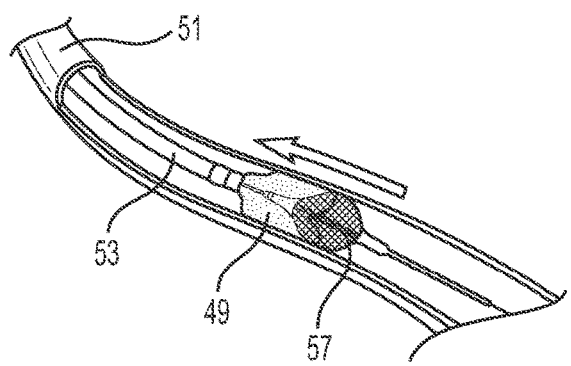
Figure 6C:
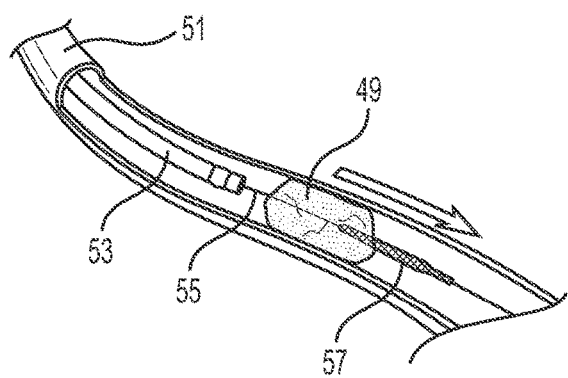
Figure 6F:
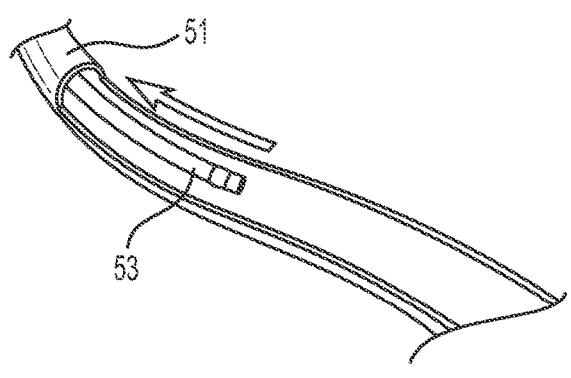

FIG. 6D shows the braided assembly 57 in an expanded configuration, sized to fit the vessel 51. The practitioner then pulls the retrieval device 55 proximally and contacts the thrombus 49 with the braided assembly 57, as shown in FIG. 6E. The thrombus 49 and braided assembly 57 are pulled proximally toward aspiration catheter 53. The aspiration catheter 53 can be connected to an external vacuum source (not shown), which enables the aspiration of the thrombus 49 into the distal end of the aspiration catheter 53. The aspiration catheter 53 is then retracted proximally, as illustrated in FIG. 6F, and removed from the body.

The ability to open the braided assembly to a range of different diameters is useful to thrombectomy procedures for multiple reasons and in multiple scenarios. The ability to custom fit the braid to a particular vessel during the procedure is preferable over introducing a braid that expands to a predetermined size, then discovering mid-procedure that it is either too small to grip the thrombus or that it is too large and has damaged the vessel. As another exemplary advantage, the level of grip between the braid and the thrombus can be optimized mid-procedure. For example, the practitioner may apply a first level of tension to the activation wire to deploy the braided assembly to a first expanded outer diameter to contact the thrombus. If the force between the thrombus and the braid is not sufficient to pull the thrombus toward the aspiration catheter, the practitioner can widen the braid to a second expanded outer diameter by applying a greater second level of tension to the activation wire. This widened diameter increases the contact force between the thrombus and the braid, such that the thrombus is more easily pulled toward aspiration catheter.

The methods can also be performed using a guidewire. For example, the guidewire can be positioned distal to the thrombus prior to advancing the distal end of the retrieval device. The retrieval device extends at least partially through a lumen of the guidewire tubing, such as in the embodiment of FIGS. 5A-5C. Together, the retrieval device and guidewire tubing are advanced over the guidewire and toward the thrombus. The guidewire extends through a separate lumen of the guidewire tubing than the retrieval device and activation wire. Once positioned, the activation wire is moved longitudinally within the retrieval device to expand the braided assembly.

Long thrombi can be addressed using braided assemblies with multiple braided sections such as the embodiment shown in FIG. 3. Movement of the slidable collar results in expansion of more than one of the braided sections, resulting in a relatively long braided assembly. In some embodiments a device with multiple, separately expandable braided assemblies, such as the one shown in FIG. 4, can be used to treat long thrombi. With separately expandable braided assemblies, as the thrombus is drawn proximally closer to the distal end of the aspiration catheter, the proximally positioned braided assembly collapses from a first expanded outer diameter to the collapsed diameter (or to a narrower second expanded outer diameter). The distally positioned braided assembly maintains an expanded outer diameter that is greater than the outer diameter of the proximally positioned braided assembly until it too is pulled into the aspiration catheter.

Various implementations of the thrombectomy device and its corresponding components are formed from one or more biocompatible materials, such as cobalt chromium, titanium and titanium alloys, stainless steel, nitinol, platinum, gold, or other metals, as well as ceramics or polymers. In addition, in some implementations, the thrombectomy device or portions thereof includes a coated material.

What is claimed is:

1. A thrombectomy device comprising:
   an aspiration catheter comprising a proximal end and a distal end;
   a retrieval device configured to extend through the aspiration catheter and exit at the distal end, the retrieval device comprising a proximal region, a distal region, and a first lumen extending therebetween;
   a braided assembly configured to disrupt and retract a thrombus to the aspiration catheter, the braided assembly extending over the distal region of the retrieval device, the braided assembly comprising a slidable collar and a braid, the braid directly attached to the slidable collar and directly attached to a fixed attachment point that anchors the braid to the retrieval device, the braid extending from the slidable collar to the fixed attachment point, and the braid comprising from 18 wires to 54 wires;
   and an activation wire extending through the first lumen of the retrieval device and through an exit point comprising a portal located in a sidewall on the distal region of the retrieval device, wherein a distal end of the activation wire is securely attached to the slidable collar;
   wherein the braid has a shape memory of a collapsed configuration; and
   wherein an expanded diameter of the braided assembly can be adjusted during retraction by varying a level of tension on the activation wire to maintain grip while retracting the thrombus.

2. The thrombectomy device of claim 1, wherein the portal is positioned beneath the braid.

3. The thrombectomy device of claim 1, wherein the retrieval device comprises a proximal hypotube and a distal support tube having greater flexibility than the proximal hypotube, and wherein a full length of the braided assembly is positioned over the distal support tube.

4. The thrombectomy device of claim 3, wherein the distal support tube is attached to a distal end of the proximal hypotube.

5. The thrombectomy device of claim 1, wherein the retrieval device comprises a proximal hypotube and a distal support tube having greater flexibility than the proximal hypotube, and wherein the exit point is defined in a longitudinally extending sidewall of the distal support tube.

6. The thrombectomy device of claim 1, further comprising a guidewire tubing, the guidewire tubing comprising a first lumen and a second lumen, wherein the retrieval device extends through the first lumen and the second lumen is configured to extend over a guidewire.

7. The thrombectomy device of claim 6, wherein the guidewire tubing is shorter than the retrieval device in the longitudinal direction.

8. The thrombectomy device of claim 6, wherein the fixed point of attachment is located on the guidewire tubing.

9. The thrombectomy device of claim 1, wherein the braid has an elliptical or a spindle shape in an expanded configuration.

10. The thrombectomy device of claim 1, further comprising at least one additional braided assembly and at least one additional activation wire, wherein each additional activation wire is attached to an additional slidable collar of an additional braided assembly.

11. The thrombectomy device of claim 10, wherein each braided assembly is separately expandable via an attached activation wire.

12. The thrombectomy device of claim 1, further comprising a proximal tensioning element, wherein a proximal end of the activation wire is attached to the proximal tensioning element.

13. The thrombectomy device of claim 12, further comprising a proximal handle, wherein the proximal tensioning element is attached to the proximal handle.

14. The thrombectomy device of claim 1, wherein the braided assembly is deployable to a first expanded outer diameter by placing a first level of tension on the activation wire, and wherein the braided assembly is deployable to a second expanded outer diameter by placing a second level of tension on the activation wire.

15. The thrombectomy device of claim 14, wherein the first level of tension is less than the second level of tension, such that the first expanded outer diameter is a maximum diameter of the braid in a partially expanded configuration, and the second expanded outer diameter is a maximum diameter of the braid in a fully expanded configuration.

16. The thrombectomy device of claim 1, wherein the braid is two-ply.

17. The thrombectomy device of claim 1, wherein all surfaces of the braid between the slidable collar and the fixed attachment point are free of direct attachments to any other component of the thrombectomy device.

18. The thrombectomy device of claim 1, wherein the braided assembly consists of the slidable collar, the braid, and the fixed attachment point.

\* \* \* \* \*

UNITED STATES PATENT AND TRADEMARK OFFICE
CERTIFICATE OF CORRECTION

PATENT NO. : 11,490,908 B2
APPLICATION NO. : 16/185319
DATED : November 8, 2022
INVENTOR(S) : Ravish Sachar et al.

Page 1 of 1

It is certified that error appears in the above-identified patent and that said Letters Patent is hereby corrected as shown below:

On the Title Page

Item (56), delete "90/51505" and insert -- 00/51505 --.

Item (57), Line 1, delete "the" before "remove".

Signed and Sealed this
Twenty-third Day of May, 2023

Katherine Kelly Vidal
*Director of the United States Patent and Trademark Office*